United States Patent
Howe et al.

(10) Patent No.: US 6,600,088 B2
(45) Date of Patent: *Jul. 29, 2003

(54) ASSAY FOR THE DETECTION OF SELECTABLE MARKER EXPRESSION IN PLANTS

(75) Inventors: Arlene R. Howe, Ballwin, MO (US); Paul C. C. Feng, Wildwood, MO (US)

(73) Assignee: Monsanto Company, St. Louis, MO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/511,826

(22) Filed: Feb. 24, 2000

(65) Prior Publication Data

US 2003/0017599 A1 Jan. 23, 2003

Related U.S. Application Data

(60) Provisional application No. 60/121,716, filed on Feb. 26, 1999.

(51) Int. Cl.⁷ ............ A01H 5/00; A01H 55/00; C12N 15/82
(52) U.S. Cl. ............ 800/278; 800/320.1; 800/312; 800/288; 424/9.1; 504/153
(58) Field of Search ............ 424/9.1; 800/278, 800/288, 312, 320.1; 504/116, 153; 435/418, 468, FOR 201

(56) References Cited

PUBLICATIONS

Stevens, PJG, 1993. organosilicone surfactants as adjuvants for agrochemicals. Pestic. Sci. 38;103–122.*

Zhou et al, 1995. Glyphosate–tolerant CP4 and GOX genes as a selectable marker in wheat transformation. Plant cell rep. 15:159–163.*

Hauptmann et al, 1988. Evaluation of selectable markers for obtaining stable transformants in the Gramineae. Plant Physiol. 86;602–606.*

Dekeyser et al, 1989. Evaluation of selectable markers for rice transformation. Plant Physiol. 90:217–223.*

Weide et al., 1989. A simple, nondestructive spraying assay for the detection of an active kanamycin resistance gene in transgenic tomato plants. Theor. Appl. Genet. 78:169–172.*

Widholm, J., 1988. Is soybean transformation finally here? Tib Tech 6:265–266.*

Klein et al, 1989. Genetic transformation of maize cells by particle bombardment. Plant Physiol. 91:440–444.*

Falco et al, "Transformation and expression of a gene for herbicide resistance in a Brazilian sugarcane," Plant Cell Reports, No. 19, p. 1188–94, (2000).

Nobre et al., "Transformation of barley scutellum protoplasts: regeneration of fertile transgenic plants," Plant Cell Reports, p. 1000–05, (2000).

Witrzens et al., "Comparison of three selectable marker genes for transformation of wheat by microprojectile bombardment," Aust. J. Plant Physiol., p. 39–44, (1998).

Robert J. Henry, "Transgenic Cereals," Advances in Cereal Transformation Technologies, American Association of Cereal Chemists (St. Paul, Minnesota), p. 191–193, (2000).

Ersa Galun and Adina Breiman, "Tools for Genetic Transformation: 3.3.3. Selectable Genes," Transgenic Plants, Imperial College Press (London), p. 62–64, (1997).

* cited by examiner

Primary Examiner—David T. Fox
Assistant Examiner—Anne Kubelik
(74) Attorney, Agent, or Firm—Thomas P. McBride

(57) ABSTRACT

Improved methods for the identification of transgenic plants containing NPTII protein are disclosed. Application of organosilicone surfactant in combination with kanamycin and/or paromomycin facilitates the identification of plants containing NPTII protein.

27 Claims, No Drawings

ASSAY FOR THE DETECTION OF SELECTABLE MARKER EXPRESSION IN PLANTS

This application claims priority to U.S. Provisional Application No. 60/121,716, filed Feb. 26, 1999, incorporated herein in its entirety.

FIELD OF THE INVENTION

The invention relates in general to methods for detecting the presence of a selectable marker in a plant. In particular, a simple and efficient method for detecting the presence of the neomycin phosphotransferase II protein in plants is disclosed.

BACKGROUND OF THE INVENTION

In the production of transgenic plants, a gene encoding a selectable marker that confers resistance to a selective agent is often included in the transformation vector to provide a means for distinguishing plant tissue that has been transformed from that which has not. The selection is typically made by growing the transformed tissue in an environment containing the selective agent and only those tissues expressing the selectable marker gene product are able to survive.

Neomycin phosphotransferase II (NPTII) is a protein of bacterial origin that confers resistance to a number of selective agents, such as kanamycin, paromomycin and genenticin, and when genetically engineered to be expressed in plant tissues, has been used as a selectable marker. Although the use of NPTII as a selectable marker to select for transformed plant tissue in the early stages of producing a transgenic plant has become routine, no efficient method for identifying NPTII-containing plants in the field has been disclosed. Typical methods involve laboratory analysis of harvested tissue from potential transgenic plants through methods including Southern blotting, immunoassays, and enzyme activity assays. These laboratory analyses are labor-intensive and time-consuming endeavors, particularly when large numbers of plants must be tested.

One method for identifying NPTII-containing transgenic tomato plants in the field has been reported. Weide et al. (*Theor. Appl. Genet.* 78:169–172, 1989) disclosed that young (three-leaf stage) transgenic tomato plants could be phenotypically distinguished from nontransgenic counterparts by spraying the plants with a solution containing kanamycin. In the Weide et al. process, trays of seedlings were sprayed with a kanamycin solution that did not include a surfactant over a three-day period, with a total application of 0.5–2.0 mg kanamycin per plant. Transgenic plants containing the NPTII protein were distinguished from non-transgenic plants in that transgenic plants did not develop bleached spots on the treated tissue within 7 days of treatment. NPTII activity in the putative transgenic plants was subsequently confirmed by a radiolabel transfer assay. This approach is disadvantageous in at least one respect in that it necessitated the use of large amounts of selective agent and a lengthy period of incubation before results were obtained and has not been shown to be an effective method for any plant other than tomato.

Thus, there exists a need for a rapid and more efficient method by which transgenic plants comprising a selectable marker may consistently be identified in the field.

SUMMARY OF THE INVENTION

This invention relates to an improved method for identifying plants expressing a selectable marker gene product, such as NPTII, and growing in the absence of a selective agent. More specifically, in one embodiment of the invention there is provided a method for detecting the presence of a selectable marker in a plant comprising contacting a composition comprising a selective agent and an effective amount of an organosilicone surfactant with putative transgenic plants, assessing the physical appearance of the plants for evidence of necrosis and/or bleaching of the treated plant tissue, and assigning the status of transgenic or non-transgenic to such plants based on the physical appearance of such plant tissue. A plant with little or no necrosis or bleaching evidences the presence of a selectable marker gene product in the plant and is determined to be a transgenic plant.

In a further embodiment of the present invention there is provided a method for detecting the presence of a selectable marker in a plant comprising contacting an effective amount of a selective agent with putative transgenic plant tissue and separately contacting an effective amount of an organosilicone surfactant with said putative transgenic plant tissue, assessing the physical appearance of the treated plant tissue for evidence of necrosis and/or bleaching of the treated plant tissue, and assigning the status of transgenic or non-transgenic to such plants based on the physical appearance of such plant tissue.

Among the many objects and advantages of the present invention include the provision of a method that utilizes a significantly reduced amount of the selective agent in the method as a result of the use of an organosilicone surfactant in cooperation with the selective agent; and the provision of a rapid, non-destructive method that may be utilized in field conditions on growing plants.

DETAILED DESCRIPTION OF THE INVENTION

It has been discovered that existing methods for detecting the presence of a selectable marker gene product in a transgenic plant growing in a non-selective environment may be improved by applying an organosilicone surfactant to the plant in addition to the selective agent or by utilizing a composition comprising a selective agent with an effective amount of an organosilicone surfactant. In accordance with the invention, significantly reduced amounts of the selective agent may be used as compared to other methods. In general, subsequent to treating the putative transgenic plant tissue with the selective agent and organosilicone surfactant (whether together or separately), the physical appearance of the treated tissue is assessed to determine is whether the treated tissue contains a selectable marker gene product or not. Treated plants that contain the selectable marker gene product will exhibit one of two phenotypes:

1) no bleaching or necrosis of the treated plant tissue; or
2) reduced bleaching or necrosis relative to that seen in a similarly treated nontransgenic plant of the same genetic background. Transgenic plants are thereby distinguished from plants that have undergone the same selective agent/organosilicone treatment and do not contain the selectable marker gene product, which display relatively more bleaching and/or necrosis of the treated plant tissue.

The nucleic acid sequence serving as the source of the selectable marker gene product functions to produce a phenotype in cells that facilitates their identification relative to cells not containing the marker. Characteristics of useful selectable markers for plants, both dicotyledonous and monocotyledonous, have been outlined in a report on the use of microorganisms (Advisory Committee on Novel Foods and Processes, July 1994). These characteristics include stringent selection with minimal contaminating nontransformed tissue, high numbers of independent transformation events without interference in subsequent regenerative steps, application to a large number of species, and availability of an assay to detect the marker. Several antibiotic and herbicide resistance markers satisfy these criteria (Dekeyser et al., Plant Physiol., 90: 217–223, 1989; Della-Cioppa et al., Bio/Technology, 5:579–584, 1987). For example, NPTII confers resistance to kanamycin, paromomycin and GENENTICIN; aph IV confers resistance to hygromycin B; aac3 and aacC4 confer resistance to gentamycin; the pat and bar genes confer resistance to phosphinothricin; and the enolpyruvylshikimate-phosphate synthase (EPSPS) and glyphosate oxidoreductase (GOX) genes confer resistance to glyphosate. In a preferred embodiment of the present invention, the selectable marker confers resistance to an antibiotic and, more preferably, the selectable marker is NPTII.

The detection method of this invention may be utilized with any species compatible with transformation with a nucleic acid sequence of interest and subsequent regeneration to form a transgenic plant. The plant may be a monocotyledonous or dicotyledonous plant. More preferably, it will be monocotyledonous of the Gramineae (Poaceae) family or dicotyledonous of the Leguminosae family. Most preferably, it will be a corn (Zea mays), wheat (Triticum), cotton (Gossypium), or soybean (Glycine max) plant.

The plant may be an Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassaya, cauliflower, celery, cherry, chicory, cilantro, citrus, clementines, coffee, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, mango, melon, mushroom, nectarine, nut, oat, oil palm, oil seed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, spinach, squash, strawberry, sugarbeet, sugarcane, sunflower, sweet potato, sweetgum, tangerine, tea, tobacco, tomato, triticale, turf, turnip, a vine, watermelon, yams, or zucchini.

A selective agent corresponding to the selectable marker gene product may be contacted with leaves of plants suspected of comprising the selectable marker. For example, expression of NPTII protein in plants confers resistance to a variety of selective agents, including kanamycin, paromomycin, ribostamycin, butirosin, geneticin, and combinations thereof. The selective agent may be any compound toxic to plants, wherein the selectable marker gene product reduces or eliminates the toxicity. The selective agent is preferably used in a quantity sufficient to make it possible to distinguish between plants comprising the selectable marker gene product and plants lacking the selectable marker gene product without causing indiscriminate toxicity.

In the preferred embodiment of the invention where NPTII is the selectable marker gene product, kanamycin is preferably used as the selective agent. Kanamycin is preferably applied to the plant in solution but may alternatively be applied in a solid or powdered form. In an alternate embodiment of the invention, paromomycin is preferably used as the selective agent corresponding to NPTII as the selectable marker. Paromomycin is preferably applied to the plant in solution but may alternatively be applied in a solid or powdered form. In a further embodiment of the invention, a combination of kanamycin and paromomycin is preferably used as the selective agent corresponding to NPTII as the selectable marker. Kanamycin and paromomycin are preferably applied to the plant in solution but may alternatively be applied in a solid or powdered form.

An organosilicone surfactant may further be contacted with the plant. Use of such a surfactant enhances the uptake of the selective agent, thereby reducing the total quantity of selective agent necessary for the assay and providing greater consistency of results. Any organosilicone surfactant compatible with the method of the instant invention may be used. The concentration of surfactant used may generally be any concentration suitable and effective to elicit a biological response in the treated plant when applied with a selective agent.

More preferably, a trisiloxane organosilicone surfactant may be used, and most preferably, the trisiloxane organosilicone surfactant SILWET-L77 (SILWET-L-77 is a registered trademark of OSi Specialties, Tarrytown, N.Y.) is used. SILWET L-77 is a nonionic silicone-based spray surfactant concentrate used in conjunction with a number of agricultural chemicals. SILWET L-77 is preferably used at concentrations of about 0.001% (v/v) to about 1.0% (v/v) in solution. More preferably, it is used at concentrations of about 0.01% (v/v) to about 0.08% (v/v) in solution, and most preferably, it is used at a concentration of about 0.04% (v/v) to about 0.07% (v/v) in solution.

Alternatively, other organosilicone surfactants may be used, including SILWET 408, SILWET Y-12808, SILWET L-7607, SILWET L-7602, SILWET L-7210, SILWET L-7002, SILWET L-720, and SILWET L-7200, all of which are registered trademarks of OSi Specialties, Tarrytown, N.Y. The organosilicone surfactants have the structure $(CH_3)_3SiO\text{—}[(CH_3)SiC_3H_6(CH_2CH_2O)_y(CH_2CH_2O)_zR]_x\text{—}OSi(CH_3)_3$, where:

| Surfactant | X | Y:Z ratio | R | Average MW |
|---|---|---|---|---|
| SILWET L-77 | 1 | 1:0 | $CH_3$ | 600 |
| SILWET 408 | 1 | 1:0 | H | 586 |
| SILWET Y-12808 | 1 | 1:0 | $COCH_3$ | 628 |
| SILWET L-7607 | 1.9 | 1:0 | $CH_3$ | 10,000 |
| SILWET L-7602 | 1 | 1:0 | $CH_3$ | 3,000 |
| SILWET L-7210 | 1 | 1:4 | H | 13,000 |
| SILWET L-7002 | 1 | 1:1 | Bu | 8,000 |
| SILWET L-720 | 1 | 1:1 | Bu | 12,000 |
| SILWET L-7200 | 1 | 3:1 | H | 19,000 |

The selective agent and organosilicone solutions described above may be contacted with the plant sequentially in any order, or the selective agent may be combined in solution with the organosilicone surfactant prior to contacting them with the plant to be tested.

The concentration of surfactant and the ratio of surfactant to antibiotic may be varied depending on plant size, plant condition, humidity, temperature, and other environmental conditions. Routine experiments may be performed to optimize the effective concentrations of surfactant and antibiotic necessary for a given plant's situation.

In particular, the stage of growth of the plant to be tested may be taken into consideration when applying the selective agent/organosilicone surfactant solutions (whether sequentially or as a combination). For example, corn development is divided into two major subdivisions; vegetative stages and reproductive stages. The vegetative stages are defined as V1 through V(n), where (n) represents the last leaf stage before tasseling occurs. The value of (n) may vary depending on hybrid and environmental differences. Each leaf stage is defined according to the uppermost leaf whose leaf collar is visible (i.e., V1=first leaf collar visible, V2=second leaf collar visible, etc.). Tested corn plants are preferably in a vegetative stage, and more preferably in V1, V2, V3, V4, V5, V6, V7, or V8. Most preferably, tested corn plants are in vegetative stage V1, V2, V3, V4, V5, or V6. Testing is done at an early stage for convenience not because the efficiency of the test is reduced. Soybean development is measured by the number of trifoliate leaves. The youngest (topmost) leaves appear to be the most sensitive to the selection agents and are therefore the preferred plant tissue to be tested in the assay.

Where the plant to be tested is a V1 or V2 corn plant, preferably about 0.0025 mg kanamycin to about 0.0125 mg kanamycin is contacted with the plant. Most preferably, about 0.01 mg kanamycin is contacted with the plant. Where the plant to be tested is a V3, V4, V5, V6, V7, or V8 corn plant, preferably about 0.005 mg kanamycin to about 0.025 mg kanamycin is contacted with the plant. Most preferably, about 0.02 mg kanamycin is contacted with the V3, V4, V5, V6, V7, or V8 corn plant. With respect to the use of paromomycin as the selective agent, where the plant to be tested is a V1 or V2 corn plant, preferably about 0.0025 mg paromomycin to about 0.0125 mg paromomycin is contacted with the plant. Most preferably, about 0.01 mg paromomycin is contacted with the V1 or V2 plant. Where the plant to be tested is a V3, V4, V5, V6, V7, or V8 corn plant, preferably about 0.005 mg paromomycin to about 0.025 mg paromomycin is contacted with the plant. Most preferably, about 0.02 mg paromomycin is contacted with the V3, V4, V5, V6, V7, or V8 plant.

When a combination of kanamycin and paromomycin is used as the selective agent and where the plant to be tested is a V1 or V2 corn plant, preferably about 0.0025 mg kanamycin to about 0.0125 mg kanamycin and 0.0025 mg paromomycin to about 0.0125 mg paromomycin are contacted with the plant. Most preferably, about 0.01 mg kanamycin and 0.01 mg paromomycin are contacted with the V1 or V2 plant. Where the plant to be tested is a V3, V4, V5, V6, V7, or V8 corn plant, preferably about 0.005 mg kanamycin to about 0.025 mg kanamycin and about 0.005 mg paromomycin to about 0.025 mg paromomycin are contacted with the plant. Most preferably, about 0.02 mg kanamycin and 0.02 mg paromomycin are contacted with the V3, V4, V5, V6, V7, or V8 corn plant.

It will be recognized that the actual concentration of the solution comprising the selective agents to be contacted with the plants in the quantities described above may be varied. Nevertheless, it is important to note that minimizing the total quantity of solution applied to the plant may improve assay sensitivity, as smaller quantities of solution are less likely to run off the plant. Therefore, the use of more concentrated solutions of selective agent is preferred. In the specific examples presented below, the selective agents are used at a concentration of 1000 mg/L in solution.

The selective agent and organosilicone surfactant may preferably be contacted with the whorl of the plant. Alternatively, they may be contacted with individual leaves, stems, or other appropriate surfaces of the plant. Most preferably, small volumes of selective agent and surfactant are contacted with the whorl of a V1, V2, V3, V4, V5, V6, V7, or V8 corn plant, from which any standing water has preferably been removed. Alternative application methods include the use of a pipetter to pipet solutions of selective agent and surfactant into the whorl, painting of leaves with solutions of selective agent and surfactant, and attachment of cotton balls soaked in solutions of selective agent and surfactant to the whorl for a period of several days. Sprays could be used, but they are environmentally less desirable. Most preferably, a pipetter will be used to pipet solutions into the whorl. For soybean and other plants without a whorl, the solution is preferably applied to the leaf.

The appearance of the treated plants is assessed following treatment. This assessment is preferably performed from three to seven days after treatment, and most preferably after five days. Treated plants lacking the selectable marker gene product display marked bleaching or necrosis, whereas plants comprising the selectable marker gene product display either reduced or no bleaching and necrosis relative to what is seen in the plants lacking the selectable marker gene product. In a preferred embodiment of the present invention where the selectable marker gene product confers resistance to an antibiotic, treatment of nontransgenic plants with a solution comprising the antibiotic may result in bleaching and/or necrosis. In particular, where the selectable marker gene product is NPTII, treatment of nontransgenic plants with kanamycin may result in bleaching, whereas treatment of nontransgenic plants with a solution comprising paromomycin may result in necrosis. The quantity of selective agent used and the quantity of selectable marker gene product in the transgenic plant may influence the appearance of the plant following treatment with surfactant and selective agent. As a consequence, appropriate selective agent and surfactant titration controls must be performed with each transgenic line of the plant to be tested and its nontransgenic counterpart.

The underlying concept and method of the instant invention may be further applied to the identification of transgenic plants that comprise other selectable markers. In these cases, a suitable quantity of the corresponding selective agent and organosilicone surfactant may be contacted with an appropriate surface of the plant by one of the methods detailed above or by other means known to those of skill in the art, and the results may be similarly assessed. A modification of the disclosed method could reasonably be expected to work for many plants that may be transformed to comprise a selectable marker.

Specific methods for transforming a wide variety of plants and obtaining transgenic plants are well documented in the literature (e.g., Gasser and Fraley, *Science* 244:1293, 1989; Fisk and Dandekar, *Scientia Horticulturae* 55: 5, 1993; Christou, *Agro Food Industry Hi Tech*, p.17, 1994; and the references cited therein). Any vector compatible with expression of a nucleic acid sequence comprising the selectable marker gene product in plants may be used in the generation of potentially transgenic plants to be tested by the method of the instant invention. The nucleic acid sequence may further comprise a gene of interest. The method of the instant invention may therefore be used in the indirect identification of plants comprising a gene of interest in addition to a nucleic acid sequence comprising the selectable marker gene product. Methods by which appropriate vectors may be constructed and used in the transformation of regenerable cell cultures, and by which such transformed cell cultures may be regenerated to form transgenic plants, are well known to those of skill in the art.

In a preferred embodiment of the invention, vectors may contain any NPTII-encoding sequences. NPTII proteins may include NPTII fusion proteins (for example, an NPTII/GUS fusion protein). The NPTII-encoding sequence may have altered codon usage to optimize translation in the plant. The codon usage may be modified to reflect monocotyledonous or dicotyledonous codon usage. For example, corn codon usage may be used for NPTII-encoding sequences to be used in transgenic corn.

In accordance with the present invention, one may transform any dicotyledonous or monocotyledonous plant with NPTII, with one of the other suggested selectable markers, or with any other selectable marker known to those of skill in the art, and subsequently use the method of the instant invention in the identification of successfully transformed plants.

The invention further encompasses kits to aid in the detection of transgenic plants containing a selectable marker gene product such as an antibiotic and more particularly an NPTII protein. The kits may comprise a first vessel containing an organosilicone surfactant; and a second vessel containing one or more selective agents to which the selectable marker gene product confers resistance in plants. Alternatively, the kit may comprise a vessel containing an organosilicone surfactant, and one or more selective agents to which the selectable marker gene product protein confers resistance in plants. The organosilicone surfactant may be any surfactant compatible with the selective agent, and preferably is SILWET L-77, SILWET 408, SILWET Y-12808, SILWET L-7607, SILWET L-7602, SILWET L-7210, SILWET L-7002, SILWET L-720, or SILWET L-7200.

Definitions

The following definitions are provided in order to aid those skilled in the art in understanding the detailed description of the present invention.

"Bleaching" refers to faded or absent leaf coloration, in spots or over the leaf surface.

"Expression" refers to the transcription of a gene to produce the corresponding mRNA and translation of this mRNA to produce the corresponding gene product, i.e., a peptide, polypeptide, or protein.

"Gene" refers to chromosomal DNA, plasmid DNA, cDNA, synthetic DNA, or other DNA that encodes a peptide, polypeptide, protein, or RNA molecule, and regions flanking the coding sequence involved in the regulation of its expression.

"Leaf collar" refers to the yellow flared band appearing at the point where the upper part of the leaf is attached to the sheath (lower part of the leaf surrounding the stem).

"Necrosis" refers to localized death within living tissue.

"NPTII" refers to a protein capable of conferring resistance to kanamycin, paromomycin, ribostamycin, butirosin, genenticin, or a combination thereof.

"Selectable marker" refers to a nucleic acid sequence whose expression confers a phenotype facilitating identification of cells containing the nucleic acid sequence. Selectable markers include those that confer resistance to toxic chemicals (e.g., ampicillin resistance, kanamycin resistance), complement a nutritional deficiency (e.g., uracil, histidine, leucine), or impart a visually distinguishing characteristic (e.g., color changes or fluorescence).

"Selective agent" refers to a substance toxic upon exposure to cells or organisms lacking a resistance mechanism.

"SILWET L-77" refers to the organosilicone surfactant having the structure $(CH_3)_3SiO—[(CH_3)RSi]_x—OSi(CH_3)_3$, where x=1 and R=—$C_3H_6O$—$(C_2H_4O)_8$—$CH_3$.

"Surfactant" refers to a surface-active agent, i.e., one which lowers surface tension at the plane of contact between phases.

"Transgene" refers to a nucleic acid coding sequence of interest and regions flanking the coding sequence involved in the regulation of its expression in the desired host.

"Transgenic" refers to organisms into which transgenes are integrated.

"Trifoliate" refers to a three-leaf arrangement on a soybean plant.

"V1, V2" etc. refer to specific stages within the vegetative period of corn development. These are defined as V1 through V(n), where (n) represents the last leaf stage before tasseling occurs and can fluctuate with environmental and hybrid differences. Each leaf stage is defined according to the uppermost leaf whose leaf collar is visible (i.e., V1=first leaf collar visible, V2=second leaf collar visible, etc.).

"Whorl" refers to a circular arrangement of three or more leaves, flowers, or other parts at the same point or level; here, the cluster of youngest leaves at the apex of the seedling.

The following examples are included to demonstrate preferred embodiments of the is invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed, while still obtaining a like or similar result and without departing from the spirit and scope of the invention.

EXAMPLES

Example 1

Determination of SILWET L-77 Concentrations

Nontransgenic corn seedlings were utilized to determine the quantity of SILWET L-77 that could be used to deliver antibiotics to a corn plant without itself causing damage to the plant. Two delivery methods were examined. 1) 1 mL of a solution of 0.01, 0.03, 0.1, 0.3, 1.0 or 2.0% SILWET L-77 was added to the whorl of each corn plant or 2) cotton rolls were soaked in a 50 mL solution of 0.01, 0.03, 0.1, 0.3, 1.0 or 2.0% SILWET L-77and then placed in the whorl of each corn plant. The whorl was tied shut with a string tag around the top of the cotton roll so the leaves remained in contact with the roll as long as possible. Plants were scored at 24 and 48 hours post application for symptoms of damage due to the surfactant. No effect of the surfactant was noticeable at 0.01% whereas plants treated with cotton rolls soaked in 0.03% SILWET L-77 had symptoms ranging from no effect to slight yellowing of the leaves. The 1 mL application of 0.03% SILWET L-77 showed no effect to very slight yellowing. Treatments utilizing 0.1% from both delivery methods had obvious yellowing. Based on the results from this study, cotton rolls soaked in 0.03% SILWET L-77 were chosen for further study to determine the amount of antibiotics to use in the assay.

Example 2

Determination of Selective Agents to be Used and Titration Thereof

Nontransgenic 3-week-old corn seedlings were assayed in order to determine the quantity of selective agent necessary in order to obtain a response. The NPTII protein confers resistance to a variety of antibiotics, including genenticin, kanamycin, and paromomycin. Cotton rolls were saturated with solutions consisting of 0.03% SILWET L-77 and various concentrations of each of these three antibiotics individually and tied to the whorl of plants to be tested. The cotton rolls were removed two days later, and the resulting bleaching and necrosis in treated plant leaves was assessed.

The concentrations of genenticin tested were 25 mg/mL, 50 mg/mL, 75 mg/mL, and 100 mg/mL. None of these treatments gave a clearly defined response, and no further experiments were performed with this antibiotic.

Kanamycin and paromomycin were both tested as described for genenticin, at concentrations of 100 mg/L, 250 mg/L, 300 mg/L, 500 mg/L, 750 mg/L, and 1000 mg/L. Slight bleaching was visible in plants treated with 250 mg/L, 300 mg/L, and 500 mg/L kanamycin solutions, and large patches of bleaching were visible in plants treated with 750 mg/L and 1000 mg/L kanamycin. Slight to moderate necrosis and some bleaching were seen in plants treated with 300 mg/L, 500 mg/L, and 750 mg/L paromomycin, and extreme necrosis and some bleaching were seen in plants treated with 1000 mg/L paromomycin. The effects of 1000 mg/L kanamycin and 1000 mg/L paromomycin singly and in combination were therefore chosen for further study and optimization to minimize the amount of antibiotic necessary in the assay.

Example 3

SILWET L-77 Concentration Studies

Ten-day-old nontransgenic corn seedlings of two genotypes were tested in an experiment designed to determine a percentage (v/v) of SILWET L-77 in solution that would not damage nontransgenic plants, but that would enhance the damaging effects of the applied selective agent. Control solutions consisted of 0.01% (v/v) SILWET L-77, 0.02% (v/v) SILWET L-77, 0.03% (v/v) SILWET L-77, 0.04% (v/v) SILWET L-77, 0.05% (v/v) SILWET L-77, and 0.06% (v/v) SILWET L-77. The six antibiotic solutions consisted of the same six concentrations of SILWET L-77 as above, with the addition of 1000 mg/L kanamycin and 1000 mg/L paromomycin. The indicated solution (10 $\mu$L) was pipetted into the whorl of each plant to be tested, and a visual assay for bleaching and necrosis was performed five days later.

For both genotypes of corn seedling, a 10 $\mu$L application of any of the control solutions (0.01%–0.06% (v/v) SILWET L-77) resulted in no damage. However, a 10 $\mu$L application of each of the antibiotic solutions described above produced moderate to extreme necrosis and bleaching in the treated leaves. A concentration of 0.06% (v/v) SILWET L-77 was chosen as the concentration best suited for causing no damage itself while most dramatically enhancing damage caused by application of solution further containing 1000 mg/L kanamycin and 1000 mg/L paromomycin.

A further experiment tested the effect of increasing the volume of solution applied to the ten-day-old seedling on assay results. Each of the solutions described above (50 $\mu$L) was applied to the whorl of the seedlings as above, and the bleaching and necrosis resulting from application of control and antibiotic solutions was subsequently assessed. In both genotypes, application of 50 $\mu$L of control solution consisting of 0.02% (v/v) SILWET L-77 or greater resulted in burning or necrosis of treated leaves, even in the absence of antibiotic. In the seedlings, no necrosis or bleaching was seen following treatment with 50 $\mu$L of the 0.01% (v/v) SILWET L-77 control solution, but some damage was seen when this quantity of control solution was applied to the seedlings. It was determined that 50 $\mu$L of solution was too much to apply to ten-day-old plants, as 10 $\mu$L of the same control solutions did not cause necrosis and bleaching following application. Consequently, it was decided that 10 $\mu$L of antibiotic or control solutions containing 0.06% (v/v) SILWET L-77 should be used with ten-day-old seedlings.

Example 4

Determination of an Appropriate Quantity of Selective Agent Used to Elicit Necrosis and Bleaching in Nontransgenic Corn Seedlings of Several Different Ages Seedlings tested were 1–3-week-old nontransgenic corn seedlings. The control solution consisted of 0.06% (v/v) SILWET L-77, while the antibiotic solution consisted of 1000 mg/L kanamycin, 1000 mg/L paromomycin, and 0.06% (v/v) SILWET L-77. The solutions were pipetted into the whorl of the seedlings of the indicated age in the indicated quantities.

For 1-week-old V1 seedlings, application of 10 or 15 $\mu$L of control solution to each plant produced no damage in treated leaves, while application of 10 or 15 $\mu$L of antibiotic solution (0.01 mg or 0.015 mg of each antibiotic, respectively) produced bleaching and necrosis. For 1week-old seedlings, application of 10 $\mu$L of control solution to each plant produced no damage in treated leaves, while application of 10 $\mu$L of antibiotic solution (0.01 mg of each antibiotic) resulted in very dramatic bleaching and necrosis.

For 2-week-old (V3) seedlings, application of 15 or 20 $\mu$L of control solution to each plant produced no damage in treated leaves, while application of 15 or 20 $\mu$L of antibiotic solution (0.015 mg or 0.02 mg of each antibiotic, respectively) produced moderate to extreme bleaching and necrosis.

For 3-week-old (V3 and V4) seedlings, application of 20 or 25 $\mu$L of control solution to each plant produced no damage in treated leaves, while application of 20 or 25 $\mu$L of antibiotic solution (0.02 mg to 0.025 mg of each antibiotic respectively) resulted in some bleaching and necrosis.

Consequently, for plants less than 11 days old, application of 10 $\mu$L of control or antibiotic solution (0.01 mg of each antibiotic for the latter) proved sufficient to induce distinguishable differences between nontransgenic and transgenic plants. For plants of 11 days or older, 20 $\mu$L of the respective solutions (0.02 mg of each antibiotic in the antibiotic solution) proved sufficient to induce distinguishable differences between nontransgenic and transgenic plants.

Example 5

Comparing Kanamycin, Paromomycin, and the Combination with and without Surfactant Nontransgenic corn plants (H99) were tested at 24 days old using 5 plants for each treatment. Plants were treated with and without surfactant at two different concentrations of paromomycin, kanamycin, and the combination of paromomycin and kanamycin. On the day of application, an antibiotic solutions consisting of 750 mg/L or 1000 mg/L paromomycin and 0.06% (v/v) SILWET L-77 was prepared, as was a control solution consisting of 750 mg/L or 1000 mg/L of paromomycin in water. Other solutions consisted of 750 mg/L or 1000 mg/L kanamycin with or without 0.06% (v/v) SILWET L-77, and 750 mg/L of both kanamycin and paromomycin or 1000 mg/L of both kanamycin and paromomycin with or without 0.06% (v/v) SILWET L-77. Antibiotic solution (20 μL) was applied to the whorl of each corn plant, from which any standing water has been removed beforehand. Seven days later the plants were observed for symptoms.

| Antibiotic treatment (20 μL) | With 0.06% SILWET L-77* | Without SILWET L-77* |
|---|---|---|
| 750 mg/L Paromomycin | 3/0/2 | 0/0/5 |
| 1000 mg/L Paromomycin | 4/0/1 | 0/0/5 |
| 750 mg/L Kanamycin | 5/0/0 | 0/1/4 |
| 1000 mg/L Kanamycin | 3/2/0 | 0/1/4 |
| 750 mg/L Paromomycin and 750 mg/L Kanamycin | 4/1/0 | 0/0/5 |
| 1000 mg/L Paromomycin and 1000 mg/L Kanamycin | 5/0/0 | 0/1/4 |

*number of plants with severe necrosis/number of plants with mild symptoms/number of plants with no symptoms Example 6

Use of a Combination of Kanamycin and Paromomycin as Selective Agent in the Identification of Corn Plants Containing NPTII Protein Corn plants (297) of 24 different lines were tested at 10 days of age for the presence or absence of NPTII protein using a combination of kanamycin and paromomycin as the selective agent. Samples of the plants were taken and analyzed by ELISA for *Bacillus thuringiensis* toxin protein (encoded on the same vector as the NPTII protein) prior to the start of the greenhouse study. On the day of application, an antibiotic solution consisting of 1000 mg/L kanamycin, 1000 mg/L paromomycin, and 0.06% (v/v) SILWET L-77 was prepared, as was a control solution consisting of 0.06% (v/v) SILWET L-77. Antibiotic solution (10 μL) was applied to the whorl of each corn plant, from which any standing water had been removed beforehand. This was more easily and more reproducibly accomplished for a large number of plants through the use of a repeat pipetter and 500 μL pipet tips. Negative controls (i.e., nontransgenic plants) were divided into two groups. Half the plants in each line tested received 10 μL of antibiotic solution, and the other half received 10 μL of control solution as an internal control for the functioning of the assay.

The treated plants were scored for the presence or absence of necrosis and bleaching five days after application of the antibiotic/SILWET L-77 solution or control solution. The scoring was done independently by four people to avoid individual bias in the assessment of damage. The greenhouse assay scores were then correlated with the *Bacillus thuringiensis* toxin protein ELISA results. The *Bacillus thuringiensis* toxin protein ELISA results correlated with the results of the whole plant assay conducted in the greenhouse scoring for 296/297 plants, giving a percentage agreement of 99.66%.

Example 7

Use of Kanamycin as a Selective Agent in the Identification of Corn Plants Containing NPTII Protein Corn plants of different lines may be tested at 10 days of age for the presence or absence of NPTII protein using kanamycin as the selective agent. Samples of the plants may be taken and analyzed by ELISA for the presence or absence of NPTII protein prior to the start of the field test. On the day of application, an antibiotic solution consisting of 1000 mg/L kanamycin and 0.06% (v/v) SILWET L-77 may be prepared, as may a control solution consisting of 0.06% (v/v) SILWET L-77 without antibiotic. Antibiotic solution (10 μL) may be applied to the whorl of each corn plant, from which any standing water has been removed beforehand. Negative controls (i.e., nontransgenic plants) may be divided into two equal groups. Half of the negative control plants may receive 10 μL of antibiotic solution, and the other half may receive 10 μL of control solution as an internal control for the functioning of the assay.

The treated plants may then be scored for the presence or absence of bleaching five days after application of the kanamycin/SILWET L-77 solution or control solution. The scoring may be done independently by several people to avoid individual bias in the assessment of damage. The field assay scores may then be correlated with the NPTII ELISA results. It is predicted that treated leaves of corn plants containing NPTII protein may also show reduced or no bleaching relative to similarly treated leaves of corn plants that do not contain NPTII protein.

Example 8

Use of Paromomycin as a Selective Agent in the Identification of Corn Plants Containing NPTII Protein Corn plants of different lines may be tested at 10 days of age for the presence or absence of NPTII protein using paromomycin as the selective agent. Samples of the plants may be taken and analyzed by ELISA for the presence or absence of NPTII protein prior to the start of the field test. On the day of application, an antibiotic solution consisting of 1000 mg/L paromomycin and 0.06% (v/v) SILWET L-77 may be prepared, as may a control solution consisting of 0.06% (v/v) SILWET L-77. Antibiotic solution (10 μL) may be applied to the whorl of each corn plant, from which any standing water has been removed beforehand. Negative controls (i.e., nontransgenic plants) may be divided into two equal groups. Half of the negative control plants may receive 10 μL of antibiotic solution, and the other half may receive 10 μL of control solution as an internal control for the functioning of the assay.

The treated plants may then be scored for the presence or absence of necrosis five days after application of the antibiotic/SILWET L-77 solution or control solution. The scoring may be done independently by several people to avoid individual bias in the assessment of damage. The field assay scores may then be correlated with the NPTII ELISA results. It is predicted that treated leaves of corn plants containing NPTII protein may show reduced or no necrosis relative to similarly treated leaves of corn plants that do not contain NPTII protein.

Example 9

Assays Using Alternative Surfactants

Assays were designed to compare the effects of SILWET surfactants L-77, L-7602, L-7210, L-7002, L-720, L-7607, and L-7200. Seedlings tested were V3 and V4 nontransgenic corn seedlings. The control solution consisted of 0.06% (v/v) surfactant, while the antibiotic solution consisted of 1000 mg/L kanamycin, 1000 mg/L paromomycin, and 0.06% (v/v) surfactant. The solutions (20 μL per plant)

were pipetted into the whorl of the seedlings. The volumes and concentrations of the various SILWET surfactants were not optimized.

Six plants were treated with antibiotic solution and were visually assessed after three days. The results were as follows:

| Surfactant | Results |
|---|---|
| L-77 | 4 plants: obvious yellowing, large necrotic patches |
| | 2 plants: small yellow patch with necrotic center |
| L-720 | 6 plants: small necrotic patch surrounded by bleaching |
| L-7002 | 5 plants: obvious necrotic patch with bleaching |
| | 1 plant: no visible bleaching |
| L-7200 | 5 plants: obvious necrotic patch with bleaching |
| | 1 plant: small necrotic patch surrounded by bleaching |
| L-7210 | 5 plants: necrotic patch and bleaching |
| | 1 plant: necrotic patch and bleaching on leaf emerging from whorl |
| L-7602 | 4 plants: necrotic patch and bleaching |
| | 1 plant: single dot of necrosis and bleaching |
| | 1 plant: small patches of necrosis and bleaching |
| L-7607 | 4 plants: obvious necrotic patch with bleaching |
| | 2 plants: small spot of necrosis and bleaching |

Control solutions containing only surfactant had no effect on V3 and V4 plants, except for a single plant observed to develop "window panes" from SILWET L-7602. "Window panes" is a symptom caused by surfactant burn and is visibly distinct from the necrosis and bleaching caused by the applied antibiotics.

Example 10

Soybean Experiments

Seventeen-day-old NPTII(+) and NPTII(−) soybean plants were treated with various combinations of kanamycin and paromomycin with and without 0.06% (v/v) SILWET L-77. The solutions were swabbed onto the trifoliate leaves with a cotton swab soaked in the solution. Ten days later the plants were observed for symptoms. Surfactant alone was used as a control; two NPTII(−) plants had slight symptomology, and none of the NPTII(+) plants had any symptoms.

| | With SILWET L-77* | | Without SILWET L-77* | |
|---|---|---|---|---|
| Antibiotic treatment | NPTII(+) | NPTII(−) | NPTII(+) | NPTII(−) |
| 1000 mg/L kanamycin and 1000 mg/L paromomycin | 0/3/5 | 5/1/0 | 0/0/8 | 0/6/1 |
| 3000 mg/L kanamycin and 3000 mg/L paromomycin | 0/7/1 | 8/0/0 | 0/2/4 | 0/7/0 |
| 5000 mg/L kanamycin and 5000 mg/L paromomycin | 0/5/0 | 8/0/0 | 0/6/0 | 0/8/0 |

*number of plants with severe necrosis/number of plants with mild symptoms/number of plants with no symptoms Example 11

Environmental Effects

Qualitative observations indicate that the application of selection agents and SILWET surfactants to plants in warm, well-lit conditions leads to more pronounced necrosis and bleaching than application under cool, dark conditions. When plants are healthy and growing well under non-stressful conditions, the effects are more pronounced and reproducible. We believe that stressful conditions such as drought, excessive heat or cold, or dark cause the stomates to close and affect the reproducibility of the assay.

All of the compositions and methods disclosed and claimed herein can be made and executed without undue experimentation in light of the present disclosure. Although the compositions and methods of this invention have been described in terms of preferred embodiments, it will be apparent to those of skill in the art that variations may be applied to the compositions and in the steps or in the sequence of steps of the methods described herein without departing from the concept, spirit and scope of the invention. More specifically, it will be apparent that certain agents that are both chemically and physiologically related may be substituted for the agents described herein, with the same or similar results. All such similar substitutes and modifications apparent to those with ordinary skill in the art are deemed to be within the spirit, scope and concept of the invention.

What is claimed is:

1. A method for detecting the presence of a selectable marker gene product in a plant growing in an environment without selective pressure, said method comprising the steps of:

obtaining a plant suspected of comprising a selectable marker encoding a NPTII protein;

contacting such plant with a composition comprising an antibiotic selective agent corresponding to said selectable marker and an organosilicone surfactant; and assessing the physical appearance of said plant for the presence of necrosis and/or bleaching of the contacted plant tissue, wherein plant tissue exhibiting reduced or no necrosis or bleaching evidences the presence of a selectable marker gene product in said plant.

2. The method of claim 1 wherein the plant is a monocotyledonous plant.

3. The method of claim 1 wherein the plant is a member of the family Gramineae.

4. The method of claim 1 wherein the plant is corn.

5. The method of claim 1 wherein the selective agent is kanamycin or paromomycin.

6. The method of claim 1, wherein the selective agent is a combination of kanamycin and paromomycin.

7. The method of claim 1 wherein the organosilicone surfactant is dissolved in a solution.

8. The method of claim 2 wherein the organosilicone surfactant is a nonionic trisiloxane organosilicone.

9. The method of claim 8 wherein the organosilicone surfactant has the formula $(CH_3)_3SiO-[(CH_3)RSi]_x-OSi(CH_3)_3$, where x=1 and R=$-C_3H_6O-(C_2H_4O)_8-CH_3$.

10. The method of claim 9 wherein the concentration of said organosilicone surfactant in the composition contacted with the plant is between about 0.01% (v/v) and about 0.08% (v/v).

11. The method of claim 9 wherein the concentration of said organosilicone surfactant in the composition contacted with the plant is between about 0.04% (v/v) and about 0.07% (v/v).

12. The method of claim 4 wherein said composition is contacted with the whorl of the corn plant.

13. A method for detecting the presence of a selectable marker gene product in a plant growing in an environment without selective pressure, said method comprising the steps of:

obtaining a plant suspected of comprising a selectable marker encoding a NPTII protein;

applying an effective amount of an antibiotic selective agent corresponding to said selectable marker and an effective amount of an organosilicone surfactant to said plant; and assessing the physical appearance of said plant for the presence of necrosis and/or bleaching of the contacted plant tissue, wherein plant tissue exhibiting reduced or no necrosis or bleaching evidences the presence of a selectable marker gene product in said plant.

14. The method of claim 13 wherein the selective agent and organosilicone surfactant are applied to said plant sequentially.

15. The method of claim 13 wherein the plant is a monocotyledonous plant.

16. The method of claim 13 wherein the plant is a member of the family Gramineae.

17. The method of claim 13 wherein the plant is corn.

18. The method of claim 13 wherein the selective agent is kanamycin or paromomycin.

19. The method of claim 13 wherein the selective agent is a combination of kanamycin and paromomycin.

20. The method of claim 18 wherein the organosilicone surfactant is dissolved in a solution.

21. The method of claim 20 wherein the organosilicone surfactant is a nonionic trisiloxane organosilicone.

22. The method of claim 21 wherein the organosilicone surfactant has the formula $(CH_3)_3SiO—[(CH_3)RSi]_x—OSi(CH_3)_3$, where x=1 and $R=—C_3H_6O—(C_2H_4O)_8—CH_3$.

23. The method of claim 22 wherein the concentration of said organosilicone surfactant in the composition contacted with the plant is between about 0.01% (v/v) and about 0.08% (v/v).

24. The method of claim 22 wherein the concentration of said organosilicone surfactant in the composition contacted with the plant is between about 0.04% (v/v) and about 0.07% (v/v).

25. The method of claim 17 wherein said composition is contacted with the whorl of the corn plant.

26. The method of claim 1 wherein the plant is soybean.

27. The method of claim 13 wherein the plant is soybean.

* * * * *

UNITED STATES PATENT AND TRADEMARK OFFICE
CERTIFICATE OF CORRECTION

PATENT NO. : 6,600,088 B2
APPLICATION NO. : 09/511826
DATED : July 29, 2003
INVENTOR(S) : Howe et al.

Page 1 of 1

It is certified that error appears in the above-identified patent and that said Letters Patent is hereby corrected as shown below:

Column 14,
Line 49, "claim 2" should read -- claim 7 --.

Column 16,
Line 1, "claim 18" should read -- claim 13 --.

Signed and Sealed this

Twenty-seventh Day of June, 2006

JON W. DUDAS
*Director of the United States Patent and Trademark Office*